(12) United States Patent
da Rocha

(10) Patent No.: US 9,040,586 B2
(45) Date of Patent: May 26, 2015

(54) VETERINARY COMPOSITIONS FOR CONTROLLING ECTO- AND ENDOPARASITES IN BOVINES, USE OF THESE COMPOSITIONS, USE OF IGR SUBSTANCES ASSOCIATED WITH MICROMINERALS, METHOD FOR CONTROLLING ECTO- AND ENDOPARASITES IN BOVINES AND KIT

(71) Applicant: Champion Farmoquimico Ltda., Anapolis-GO (BR)

(72) Inventor: Flávio Alves da Rocha, Anapolis (BR)

(73) Assignee: Champion Farmoquimico Ltda., Anapolis-GO (BR)

( * ) Notice: Subject to any disclaimer, the term of this patent is extended or adjusted under 35 U.S.C. 154(b) by 6 days.

(21) Appl. No.: 13/648,610

(22) Filed: Oct. 10, 2012

(65) Prior Publication Data
US 2014/0066514 A1    Mar. 6, 2014

(30) Foreign Application Priority Data
Aug. 28, 2012  (BR) ................. 11 2012 0216066

(51) Int. Cl.
*A01N 47/34*        (2006.01)

(52) U.S. Cl.
CPC .................................... *A01N 47/34* (2013.01)

(58) Field of Classification Search
CPC ......................................................... A01N 47/34
See application file for complete search history.

(56) References Cited

U.S. PATENT DOCUMENTS

| 4,166,107 | A | 8/1979 | Miller et al. |
| 4,281,003 | A | 7/1981 | Miesel |
| 7,348,019 | B1 * | 3/2008 | Murphy et al. ............... 424/410 |
| 2003/0007998 | A1 * | 1/2003 | Block et al. .................. 424/442 |

* cited by examiner

*Primary Examiner* — Wu-Cheng Winston Shen
*Assistant Examiner* — Christopher R Stone
(74) *Attorney, Agent, or Firm* — Kilyk & Bowersox, P.L.L.C.

(57) ABSTRACT

Veterinary compositions are described for controlling ecto- and endo-parasites in animals, such as bovine. The compositions contain an IGR compound(s) or a benzoyl substituted urea(s) along with a mineral mix and at least one carrier.

16 Claims, No Drawings

VETERINARY COMPOSITIONS FOR CONTROLLING ECTO- AND ENDOPARASITES IN BOVINES, USE OF THESE COMPOSITIONS, USE OF IGR SUBSTANCES ASSOCIATED WITH MICROMINERALS, METHOD FOR CONTROLLING ECTO- AND ENDOPARASITES IN BOVINES AND KIT

FIELD OF INVENTION

The present invention regards a veterinary composition, preferably in the form of dust or powder, as an IGR (insect growth regulator) compound-based feed and/or mineral supplementation additive (rock salt, mineral salt, vitamin concentrates, among others), or particularly substituted benzoyl urea-based, associated with microminerals, to simultaneously control ecto- and endoparasites, preferably cattle ticks and horn flies (ectoparasites) and *Haemonchus* spp. (endoparasite) in bovines.

INVENTION BACKGROUND

Cattle Tick

Cattle tick (*Rhipicephalus [Boophilus] microplus*) is the main ectoparasite of cattle present in subtropical and tropical regions.

Cattle Tick Cycle

This arthropod's life cycle can be divided in two phases: parasitic and free-living.

Newly attached seed ticks (larvae) start feeding and molt twice, to become nymphs and then adults. Each developmental stage (larva, nymph and adult) feeds only once, but the feeding takes place over several days. Adult male ticks become sexually mature after feeding, and start mating with feeding females. Each female tick ingests around 3 mL of blood during its feeding life, and converts 60% of its body mass in eggs. Therefore, a group of 3 grams of engorged females (8 to 10 ticks) produces around 1.8 grams of eggs, where each gram represents 20,000 larvae (GONZÁLES, J. C; O controle do carrapato do boi. Porto Alegre: Sulina, 1993 104 p.) A single adult female tick is capable of depositing up to 3,000 eggs in the environment.

The free-living stage starts when the engorged female tick drops to the ground and looks for a suitable place to deposit its eggs. The eggs laid on the ground will hatch and the larvae will start looking for a host.

This stage usually takes between 28 and 51 days to be completed, but it can take as long as 300 days. Besides that, cattle tick larvae can survive as long as 6 months without feeding.

Economic Losses Caused by the Cattle Tick

Heavy tick burdens on livestock animals can decrease production and damage hides. The cattle tick can also transmit babesiosis (caused by the protozoa parasites *Babesia biqemina* and *Babesia bovis*) and anaplasmosis (caused by *Anaplasma marginale*).

Babesiosis or "cattle fever" was eradicated from the U.S. between 1906 and 1943, but before that babesiosis cost the U.S. an estimated $130.5 billion. Although a permanent quarantine zone is maintained along the Mexican border to prevent their reintroduction into the U.S., cattle ticks are finding new ways of crossing the zone unhindered, like the white-tailed deer (POUND, J M; GEORGE, J E; KAMMLAH, D M; LOHMEYER, K H; DAVEY R B; Evidence for role of white-tailed deer (*Artiodactyla: Cervidade*) in epizootiology of cattle ticks and southern cattle ticks (*Acari: Ixodidae*) in reinfestations along the Texas/Mexico border insouth Texas: a review and update. J Econ Entomol. 2010 April; 103(2): 211-8).

Other losses include, directly, as consequences of tick bites: irritability, blood loss leading to weight loss and reduced dairy production, secondary infestations (myiasis) and damaged hides. Among indirect losses are increased labor costs, cost of acaricides, environmental losses due to the use of such substances and its residues in animal products (ANDREOTTI & GOMES, 2003) since the non-compliance of the withdrawal period forbids human consumption (FURLONC & PRATA, 2006), and the risk of intoxication by long time exposure, that could lead to teratogenic or/and carcinogenic effects on man (ROJAS et al., 2000 quoted by SILVA, 2001).

Cattle Tick Control Products

Nowadays, cattle tick control is a real challenge to livestock economics. This procedure demands that the cattle is gathered in the field and then herded to the corral.

A roundup is an extremely laborious activity that involves many people and has a long duration. During a roundup, animals cannot feed, are subjected to stress, can be harmed by handlers or by escape attempts, and suffer considerable weight loss.

Beyond all those losses, the herding of animals to the corral leads to a disorganization of their activities (PARANHOS DA COSTA & NETO, 2003), and that can lead to weight loss up to 15 kg per roundup (ARENALES, 2004). Stressful roundup activities raise the risk of accidents, which may lead to bruised carcasses (PARANHOS DA COSTA et al., 2004).

The existing products for cattle tick control can be classified in families or chemical groups. Acaricides can work in two ways:

a—Contact acaricides:

Applied through mean of pulverization, immersion or pour-on, and are divided in 5 groups or families.

a.1) Organo-phosporous: Oldest group of acaricides still in the market for cattle tick control, with small residual power, and no longer in use by the majority of ranchers due to the belief that cattle ticks have developed strong resistance to them.

a.2) Amidine: this group followed organo-phosporous substances and is characterized by a stronger residual power than the first, which allows for longer intervals between treatments. It has great acceptance among ranchers and it's still one of the mostly used acaricide groups, even after 20 years from its debut.

a.3) Synthetic pyrethroids: chemical group with lots of subfamilies, the most common being Deltamethrin, Cypermethrin and Alfamethrin. Their stronger residual power favored the development of resistance among tick populations against this group. In the hope of prolonging the usefulness of this group, new formulations were developed, in which pyrethroids were associated to organo-phosporous as a way of boosting its efficacy:

a.4) Phenylpyrazoles: Similar in effect to the avermectins, i.e., the substance acts on the tick's nervous system, paralyzing it. However, it has the disadvantage of not being indicated for use on lactating cows. It's mainly applied as pour on.

a.5) Cymiazoles: an iminophenyl thiazolidine derivative, active against mites and ticks. Sometimes associated with synthetic pyrethroids (on spray form), its use is permitted on lactating cows, with no withdrawn period needed. In beef cattle, 3 days withdrawal prior to slaughter must be observed.

a.6) Naturalyte: the most recent chemical group, which has Spinosad as its active compound. It's obtained from the fermentation of an actinomycete fungus, and can be used on lactating cows.

b—Systemic acaricides:

Applied through means of injections or pour on, substances in this category are metabolized by the animal's organism and carried on the bloodstream before being excreted.

b.1) Macrocyclic Lactones: This chemical group comprehends avermectins and milbemycins, or chemical derivatives thereof, of soil microorganisms belonging to the genus *Streptomyces*. The avermectins in commercial use are ivermectin, abamectin, doramectin, eprinomectin, and selamectin. Commercially available milbemycins are milbemycin oxime and moxidectin. The macrocyclic lactones have a potent, broad antiparasitic spectrum at low dose levels. They are active against many immature nematodes (including hypobiotic larvae) and arthropods (like cattle ticks). The published literature contains reports of use to treat infections of >300 species of endo- and ectoparasites in a wide range of hosts. Moreover, a single therapeutic dose can persist in concentrations sufficient to be effective against incumbent nematode infections for prolonged periods after treatment. As a downside, most of the substances in this group can't be used on lactating cows.

b.2) Insect Growth Regulators (IGR): Substances (chemical) that inhibits the life cycle of an insect. Unlike classic insecticides, IGRs do not affect an insect's nervous system and are thus more worker-friendly within closed environments. IGRs are also more compatible with pest management systems that use biological controls. In addition, while insects can become resistant to insecticides, they are less likely to become resistant to IGRs. On ticks, IGRs inhibit molting and hatching of eggs, therefore controlling infestations on the environment.

Another great disadvantage of existing products is that lots of them leave toxic chemical residues on both beef and dairy cattle. Some examples below:

| Product commercial name | Lab | Active ingredient (A.I.) | A.I. concentration | Withdrawal period Meat | Withdrawal period Milk |
|---|---|---|---|---|---|
| Triatox | Intervet | Amitraz | 12.5% | 15 days | 24 hours |
| Topline | Merial | Fipronil | 1% | 100 days | Do not apply on lactating cows |
| Acatak | Novartis | Fluazuron | 2.5% | 42 days | Do not apply on lactating cows |
| Dectomax Injectable | Pfizer | Doramectin | 1% | 35 days | Do not apply on lactating cows |
| Cydectin Injectable | Virbac | Moxidectin | 1% | 28 days | Do not apply on lactating cows |
| Ivomec Gold Injectable | Merial | Ivermectin | 3.15% | 122 days | Do not apply on lactating cows |
| Avotan L.A Injectable | Intervet | Abamectin | 1% | 42 days | Do not apply on lactating cows |

Contamination takes place through absorption of acaricides' active ingredients by the treated animals' organisms.

The object of the present invention uses active ingredients of extremely low toxicity that are poorly absorbed by the treated animals, and rapidly eliminated after that, which avoids the contamination described above.

The table below shows the median lethal dose (LD50) of the most commonly acaricides in use:

| Product | Class | Oral LD50 (in grams per kilo) |
|---|---|---|
| Cypermethrin | Pyrethroid | 250 mg/kg |
| Deltamethrin | Pyrethroid | 130 mg/kg |
| Dichlorvos | Organo-phosporous | >50 mg/kg |
| Chlorpyrifos | Organo-phosporous | 95 to 270 mg/kg |
| Abamectin | Macrocyclic Lactones | 10 mg/kg |
| Ivermectin | Macrocyclic Lactones | 52 mg/kg |
| Doramectin | Macrocyclic Lactones | 50 to 200 mg/kg |
| Fipronil | Phenilpyrazole | 97 mg/kg |

The median lethal dose of Diflubenzuron, one of the active ingredients of the present invention, is 4,640 mg/kg, i.e., dozens of times safer than the commonly used active ingredients.

Some IGRs compounds are used on oral compositions against ectoparasites, but in single dose form. This method requires high concentrations of active ingredients to reach the desired effect. The present invention works in a different way, since it's offered daily in small amounts. This method leads to a safer and more efficient action.

Advantages of the Present Invention

The object of the present invention represents an innovation, since it helps to avoid all the inconveniences described above, particularly in relation to costs of cattle handling or to the absorption of chemical residues in the treated animals' organisms, since it refers to a veterinary composition, such as in dust form, ready to use as a feed additive, to provide efficient ectoparasite control with minimum toxicity levels, since it has specific and selective effect, passing through the treated animals' bloodstream and acting exclusively on interrupting the synthesis of chitin, the main component of the exoskeletons of ticks, not interfering in any way on the well-being of the treated animals' organisms.

Horn Fly

The horn fly is one of the most serious and injurious pests of cattle. Horn flies pierce the skin of cattle to suck blood often taking up to 20 blood meals per day. The resulting pain and annoyance interferes with feeding, resting and the other normal activities of cattle.

Horn Fly Cycle

The horn fly is about ½ to ⅓ the size of the common house fly. Both male and female horn flies are hematophagous, and they mate while on the host. The adult female deposits its eggs exclusively in fresh cattle manure (within 10 minutes of dropping). The eggs are reddish-brown and difficult to detect in the manure.

The eggs hatch within 18 hours to the first stage larva or maggot. The maggot feeds in the dung developing through 3 instars in 3-5 days. Pupation normally requires 3-5 days. When the adults emerge from the pupal case, it takes 3 days for the complete maturation of the reproductive organs for egg production. The total life cycle from egg to egg-laying adult takes from 10 to 14 days.

Female flies can lay 20-30 eggs at one time and up to 400 eggs during their lifetime. Horn flies rarely leave the host except to deposit the eggs on dung. Most of the adult life is spent on the host.

Economic Losses Caused by the Horn Fly:

Horn flies pierce the skin of cattle to suck blood and may take up to 20 meals per day. The irritation and blood loss cause cattle to lose 0.3 to 0.5 lbs. per day and for dairy animals cause lower milk production. Large populations of horn flies may cause open sores on the head and underline which can predispose their hosts to secondary infections of both disease and parasites. Because of their piercing-sucking mouthparts, horn flies are suspected of mechanically transmitting anthrax and other diseases within a herd.

Horn fly numbers of 50 or more per lactating dairy cow or 200 or more per beef cow are considered to be of economic importance. Research has shown that a calf infested with more than 200 horn flies will gain 15 to 50 pounds less than normal from birth to weaning and sale (about 4 to 6 months). Horn flies can also reduce milk production in dairy cows by up to 20 percent. Extreme numbers of 10,000 to 20,000 flies per animal have been reported and could make blood loss alone (0.5 gal/month) an important factor in reduced production.

Production is consistently lower on untreated animals. The cost of treatment is nominal compared to the increased production realized by treatment.

Horn Fly Control Product

Horn flies remain on the host except when laying eggs or migrating to new hosts. Their close association with cattle makes them susceptible to chemical control measures. Insecticides tram pyrethoid and organo-phosporous groups are commonly used.

Ear tags, forced-use dust bags, sprays or dips may be used successfully. Dust bags may be hung in exit alleyways from barns or placed between pasture and water or feed. Dust bags will provide effective control only if they are hung where cattle are forced to dust. Back rubbers can also give control but are usually less successful on horn flies.

Sprays may also be used for horn fly control. Residual sprays are to be applied at 1-2 qt/animal at 150 to 200 psi to gain complete coverage of animal and penetration to the skin. Animals are supposed to be treated in small groups so that all animals are covered.

The main disadvantage of these methods is that they require the herd to be brought into the corral. As discussed above, handling the animals inside the corral is a major source of costs to the rancher. Its avoidance would undoubtedly represent economic relief.

The products in use nowadays for horn fly control are divided in the following groups, by means of appliance:

a) Spray: Insecticide sprays come as ready-to-use or are diluted with water before applying. It is important to get complete coverage of each animal with the spray and penetration to the skin. Animals can be treated in small groups to assure complete coverage.

More handling is required using sprays since they must be confined in a corral so that they can be sprayed thoroughly. While sprays are generally easy to apply, several applications may be needed because their duration of control is often limited (3 to 4 weeks).

b) Pour-on: These insecticides are ready-to-use formulations that are applied in measured doses to animals based upon body weight. Most function as contact insecticides. Typically, they provide fly reduction for several weeks, so they must be re-applied periodically. The duration of control will vary with weather and other factors so re-apply when fly numbers build back up to about 50 per side but no sooner than the label instructions allow.

c) Ear-tags: Insecticide ear tags contain one or more insecticides embedded in a plastic matrix. Movement of the tag while the animal is moving or grooming slowly releases small quantities of insecticide over a period of time (weeks) which travels through the hair coat of the animal. Generally, ear tags are more effective against insects such as horn flies that spend the majority of their life on the animal and are less effective or ineffective against insect pests that are on the animal for a short period of time (e.g., mosquito, deer fly, horse fly). When ear tags were first introduced in the late 1970s they were very effective against horn flies, providing season-long control. However, this initial success was short-lived. Within a few years, horn flies developed resistance to pyrethroid insecticides used in the tags and many producers stopped using them, choosing to go back to dust bags, oilers or feed additives or do nothing at all. Animal health companies have developed different insecticide chemistry to combat the resistance problem. As a result, there are many different types of tags on the market with different insecticides. Currently, there are ear tags on the market that contain one or more synthetic pyrethroids, one or more organophosphate insecticides, or a combination of a synthetic pyrethroid and an organophosphate. There are also ear tags that contain endosulfan, an organochlorine insecticide, and abamectin, an insecticide derived from the soil bacterium *Streptomyces avermitilis*.

d) Dust-bags and back rubbers: Dust bags contain insecticide dust that filters through the bottom of the bag when cattle contact the bag while passing under it. The best horn fly control is achieved when cattle are forced to pass under the bags on their way to get water, feed or mineral. This is accomplished by fencing the water tank and suspending the dust bags in the entrance-exit gate. Forced-use of dust bags is often not practical with range cattle because they may obtain water from stock ponds or streams. In this case, dust bags can be placed at locations where cattle loaf during the day to be used free-choice. In some cases older cattle and bulls will dominate a dust bag so only a few animals ore treated. Bags should be inspected regularly and recharged with insecticide dust when necessary.

A back rubber consists of a chain or chains wrapped in burlap and secured with wire. The burlap is treated with an insecticide designed for back rubbers and is diluted with No. 2 diesel fuel or commercial back rubber oil. Back rubbers, like dust bags, work best in a forced-use situation.

e) Oral larvicides (feed additives) and boluses: Oral larvicides (feed additives) are insecticides that are incorporated into mineral blocks, tubs or loose mineral. The insecticide is passed out in the manure and kills fly larvae that develop in manure. Oral larvicides are effective when consumed in sufficient quantities all season long. A bolus containing an insect growth regulator is also available. The bolus enters the cow's reticulum and slowly releases the insecticide which passes out with the manure.

The products listed above (with the exception of oral additives and boluses) have reduced efficiency, because they are capable of affecting only the adult horn fly population, since they're applied in a topical fashion.

Horn flies don't deposit eggs on the host's skin, only on their feces. Therefore, those products have no preventive action against the development of the larvae.

As for the bolus, its application requires specific tools (like the balling gun) and experience, since failure to apply it correctly can lead to the animal suffocating. Additionally, introducing the gun and administering the bolus for each head of cow is an extremely time-consuming and costly activity.

Advantages of the Present Invention

The object of the present invention represents an innovation, since it helps to avoid all the inconveniences described above, particularly in relation to costs of cattle handling or to the absorption of chemical residues in the treated animals' organisms, since it refers to a veterinary composition in dust form, ready to use as a feed additive, to provide efficient ectoparasite control with minimum toxicity levels, since it has specific and selective effect, passing through the treated animals' bloodstream and being excreted among the feces, where it will act exclusively on interrupting the synthesis of chitin, the main component of the exoskeletons of horn flies, not interfering in any way on the wellbeing of the treated animals' organisms.

U.S. Pat. No. 4,100,107 describes bolus formulations of slow release containing regulators for the development of insects with a mixture of wax, grease, and barium sulfate, useful for the control of arthropods in manure. As for the present invention, it refers to a veterinary composition, such as in dust form, ready to use as a feed additive to be used mixed with rock salt, mineral salt or feeds.

There are some excerpts throughout the patent that point to pure IGR forms as feed additives (instead of compounds containing IGR as active ingredients), which happens to be a somehow inefficient way of treating cattle. The addition of pure form IGR can undermine insect control efficiency. In this regard, the object of the present invention makes use of various pharmacotechnical resources to boost the active ingredient's efficiency, as follows: smaller particle size, which helps on mixing the compound in the cattle feed or salt, presence of tensoactives, which allow for a better absorption of the active ingredient on the feed bolus and better spreading on the feces, etc.

U.S. Pat. No. 4,281,003 describes oral administration (which includes boluses and other means of offering medication orally to the animal, but not specifically on feed-through methods) of insecticides for insect control on cattle feces. It mentions Diflubenzuron, without suggesting or even referring to the advantages or components of the present invention's composition formula.

*Haemonchus* Spp.

*Haemonchus* spp., also known as red stomach worm, wire worm or Barber's pole worm, is a very common parasite and one the most pathogenic nematodes of ruminants. Adult worms are attached to abomasal mucosa and feed on the blood. This parasite is responsible for anemia, bottle jaw, and death of infected sheep, goats and calves, mainly during summer months in warm, humid climates Haemonchosis Cycle The adult female worm can release between 5,000-10,000 eggs which will be passed out in the feces. The oocyte is yellowish in color. The egg is approximately 70-85 $\mu$m long by 44 $\mu$m wide, and the early stages of cleavage containing between 16-32 cells. The adult female is 18-30 mm long and is easily recognized by us trademark "barber pole" coloration, the red and write appearance is due to the fact the *Haemonchus* spp. is a blood feeder and is due to the white ovaries that coil around the intestines which are filled with blood. The male adult worm is much smaller at 10-20 mm long and displays the distinct feature of a well-developed copulatory bursa, containing an asymmetrical dorsal lobe and a Y shaped dorsal ray.

After egg shedding, eggs develop in moist conditions in the feces and continue to develop into the L1 (rhabditiform), and L-2 juvenile stages by feeding on bacteria in the dung. The L-1 stage usually occurs within 4-6 days under the optimal conditions of 24-29° C. The L-2 rhabditform sheds its cuticle and then develops into the L-3 filiariform infective larvae. The L-3 have a protective cuticle, however under dry hot conditions will not survive long. The L-3 then crawl up the blades of wet grass and wait to be ingested by a grazing animal. Sheep, goats and other ruminants become infected when they graze and eat grasses containing the L3 infecting larvae. The infecting larvae pass through the first three stomachs to reach the abomasum. There the L-3 sheds its cuticle and burrows into the internal layer of the abomasum where they develop into L-4, usually within 48 hours, or pre-adult larvae. The L-4 larvae then molt and develop into the L-5 adult form. The male and female adults mate and live in the abomasum, where they feed upon the blood.

Damage Caused by *Haemonchosis*

The nematode piercing the abomasum causes a number of significant complications in the infected ruminants that can lead to death. The infected animals can display severe dehydration, diarrhea, unthrifty appearance, lethargy, depressed low energy behavior, rough hair coat and uncoordinated movements. Furthermore, significantly reduced growth and poor reproductive performance has been observed. The accumulation of fluid in the abdomen, gut wall, thoracic cavity and submandibular tissue—a phenomenon commonly called "bottle jaw", also is a common association with this infection Severe blood loss, white mucous membranes, and anemia/ low PCV are common complications of the infection.

The infection, called Haemonchosis, causes large economic losses for farmers around the world, especially for those living in the warmer climates. Anthelmintics are used to combat these and other worm infections for a long time, but resistance of the parasites against these chemicals is growing.

To HOSSETTO (2000), dairy cattle with high incidence of worms can show a substantial loss in milk yield, up to 25% of the daily production. A 5%-10% raise in the annual mortality rate may be expected (Marques, 2003), especially among calves, as well as 12% less births per year (FADIL, n/d.).

*Haemonchus* Control Products

Existing anthelmintics work by killing the adult forms and immature species by means of its toxic effect, although they don't possess enough residual power that leads to re-infestation cycle elimination. So after 28-35 days an estimated 70% of worm infestation will be back. Moreover, existing anthelmintics leave toxic residues on beef and milk of the treated animals, and are more likely to be affected by anthelminthic resistance.

Parasitic resistance to anthelmintics is a phenomenon whereby members of a population are selected and become dominant after constant use of a chemical compound. The diagnosis will be positive for "resistance" when a certain drug that used to show 99% efficacy over the parasite burden reduction starts showing less than 95% efficacy against the same parasites after certain period of time (MOLENTO, 2004).

In recent years, the problem of anthelmintic resistance has reached new heights where it can no longer be ignored as a major issue in the control of parasites of livestock. It is an inconvenient truth that reports of resistance are no longer noteworthy; anthelmintic resistance is the status quo. In many parts of the world multiple-resistant parasites are highly prevalent, and it is no longer uncommon to find sheep or goat farms where resistance exists to all available anthelmintic drugs (Cezar et al., 2010; da Cruz et al., 2010; Howell et al., 2008). In general, levels and spectrum of anthelmintic resistance are less severe in parasites of horses and cattle, but the same problems exist and seem to be worsening (Kaplan, 2004; Kaplan et al., 2004; Soutello et al., 2007; Suarez and Cristel, 2007; Traversa et al., 2009; Waghorn et al., 2006a). Thus, in some regions, high levels of multiple-drug resistance threaten the health and productivity of these species as well.

Until the recent introduction of monepantel (Kaminsky et al., 2008) in New Zealand and the United Kingdom, there had not been a new class of anthelmintics delivered to the livestock market since ivermectin almost 30 years ago. This new drug and others, such as derquantel (Little et al., 2010), may offer a temporary reprieve from the problems created by mounting failures of older anthelmintics. However, the development of new anthelmintic drug classes is not likely to solve the problem of anthelmintic resistance. The great cost associated with the development of new drugs and the trends of reduced levels of investment into new animal drug research over the past few decades make it extremely unlikely that we are entering a new phase where a continuous supply of new anthelmintic compounds will follow (Geary et al., 2004).

Over the past decade there have been increasing numbers of reports of anthelmintic resistance in gastrointestinal nematodes of cattle worldwide, and most of these concern resistance to the avermectin/milbemycin drugs (Anziani et al., 2001, 2004; Condi et al., 2009; Demeler et al., 2010; Edmonds et al., 2010; Familton et al., 2001; Fiel et al., 2001; Gasbarre et al., 2009; Mejia et al., 2003; Mena et al., 2008).

The most comprehensive studies investigating the prevalence of anthelmintic resistance in cattle parasites have been performed in New Zealand (Waghorn et al., 2006a) and in South America (Soutello et al., 2007; Suarcz and Cristel, 2007). In all three studies injectable avermectin/milbemycin products were used, with data indicating that resistance is becoming a very serious problem in these regions. In the North Island of New Zealand a reduction in FEC of ≥95% was demonstrated on only 7% of beef cattle farms (4/61) for all anthelmintics tested (albendazole, levamisole, ivermectin). Resistance to ivermectin, albendazole, and to both ivermectin and albendazole was reported on 92, 76, and 74% of farms, respectively. Levamisole resistance was uncommon; resistance was evident on only 6% (4/62) of farms. Based on coproculture and larval identification. *Cooperia* spp. were the most prevalent genera in resistant populations, and on most farms *Cooperia* were resistant to both ivermectin and albendazole. No cases of levamisole resistance in *Cooperia* were detected.

However, resistance was detected in *Ostertagia* spp. to all 3 drugs; resistance was evident on 9, 35, and 9% of farms for ivermectin, albendazole and levamisole, respectively.

In Sao Paulo state, Brazil, 23 of 25 cattle farms had <90% reduction in FEC following treatment with ivermectin, and on 19 of these farms reductions in FEC were <50% (Soutello et al., 2007). Following treatment with albendazole or levamisoie, 5 and 2 of 25 farms, respectively had reductions in FEC or <90%. Moxidectin was effective on all farms; 19 farms had a FECR of 100%, and on the other 6 farms FECR ranged from 90% to 97.2%. Multiple resistance (FECR <90%) to albendazole and ivermectin was observed on three farms and to albendazole, levamisoie, and ivermectin on an additional two farms. The predominant genera infecting these cattle were *Cooperia* spp. And *Haemonchus* spp. and both genera were consistently found associated with resistance. In addition there was evidence on two farms for moxidectin-resistance in *Oesophagostomum* spp. Resistance in *Oesophagostomum* spp. was subsequently confirmed using FECRT combined with a controlled efficacy test (using injectable moxidectin) on a cattle farm in Brazil (Condi et al., 2009). An interesting observation in this study was that 98.5% of the *Cooperia* spp. females recovered at necropsy (14 days after treatment) from the control animals had eggs inside the uterus, as compared to only 48.2% of the females recovered from the moxidectin-treated group (P<0.001). A temporary suppression of egg output by worms surviving moxidectin treatment has been reported previously in sheep (Sutherland et al., 1999). These data indicate that moxidectin treatment may cause a temporary suppression in egg output; suggesting that FECRT data from moxidectin (and other macrocyclic lactone drugs) should be interpreted with caution to avoid mis- or under-diagnosis of anthelmintic resistance. These data also suggest that 14 days may not be a sufficient interval following moxidectin treatment for post-treatment feces collection, and that 17-21 days may be preferred.

To apply any of these anti-parasite drugs it's necessary to gather the herd and lead them to the corral. The losses related to this activity have already been described above.

The existing anthelmintics are known to leave residues in beef and milk, being necessary to establish their withdrawal periods.

| Commonly Used Deworming Products | | | | |
|---|---|---|---|---|
| | | | Warnings and Withdrawals** | |
| Type | Trade Name | Active Ingredient | Dairy & Milk | Beef & Slaughter |
| Block | SafeGuard Cattle Block | Fenbendazole | Note 1 | 11 d |
| Drench | Prohibit | Levamisole | Note 1 | 48 h |
| | Synanthic 9.06% | Oxfendazole | Note 1 | 7 d |
| | Synanthic 22.5% | Oxfendazole | Note 1 | 7 d |
| | Panacur | Fenbendazole | 0 | 8 d |
| | SafeGuard | Fenbendazole | 0 | 8 d |
| | Valbazen | Albendazole | Note 1, 2 | 27 d Note 2 |
| Feed additives | Safeguard | Fenbendazole | 0 | 13 d |
| | Rumatel | Morantel Tartrate | 0 | 14 d |

-continued

Commonly Used Deworming Products

| Type | Trade Name | Active Ingredient | Warnings and Withdrawals** | |
|---|---|---|---|---|
| | | | Dairy & Milk | Beef & Slaughter |
| Injectable | Levamisol | Levamisole | Note 1 | 7 d |
| | Ivermectin Containing | Ivermectin | Note 1 | 35 d |
| | Ivomec Plus, Noromectin Plus | Ivermectin/ Clorsulon | Note 1 | 49 d |
| | Dectomax | Doramectin | Note 3 | 35 d |
| | Cydectin | Moxidectin | Note 1 | 21 d |
| Paste | Panacur | Fenbendazole | 0 | 8 d |
| | SafeGuard | Fenbendazole | 0 | 8 d |
| Pour-on | Ivermectin Containing Pouron | Ivermectin | Note 1 | 48 d |
| | Eprtnex | Eprinomectin | 0 | 0 |
| | Dectomax Pouron | Doramectin | Note 3 | 45 d |
| | Cydectin Pouron | Moxidectin | 0 | 0 |
| Mineral | SafeGuard Mineral dewormer | Fenbendazole | 0 | 13 d |

*Local feed dealerships may independently market feed mixes and blocks containing additive products.
Note 1:
Not to be used on dairy cattle of breeding age.
Note 2:
Not to be used during the first 45 days of pregnancy or for 45 days after bull removal.
Note 3:
Safe in dairy heifers up to 20 months of age.
**Withdrawals are subject to change.

Advantages of the Present Invention

Knowing that iron is the oxygen carrier in the organism, and that all nematode larvae have aerobic breathing equipment, it has been observed that worm expelling is a consequence of high oxygen levels in their habitat, naturally anaerobic. Such increased oxidant tension gives these nematodes a sense of security and they feel compelled to loose themselves from the mucous membranes, nullifying the respiratory tropism, which is paramount to a low-oxygen level habitat. The worm feeds on the cells of the gastrointestinal wall.

The environment in which worms live, stomach and intestine, are anaerobic. When in contact with the gastrointestinal environment, our invention releases oxygen. In the presence of oxygen, the worm releases itself from the stomach and/or intestine walls and blends in the gastrointestinal contents. In this state, it will be surrounded by waste until the animal excretes it.

This particular mechanism doesn't lead to resistance among parasites, which is the major issue regarding common anthelmintic drugs.

DESCRIPTION OF THE INVENTION

Different from the prior art, including commercial uses and available uses in the literature, the present invention refers to a veterinary composition. The composition can be in solid form, such as a powder, pellets, blocks, and the like. The composition can be a powder such as in a dust form. The composition can be a flowable powder. The composition can be added in the feed or mineral supplement consumed by animals, such as, but not limited to, bovines. The composition can be simultaneously efficient/effective against ecto- and endoparasites, such as but not limited to *Haemonchus* spp., *Rhipicephalus* (*Boophilus*) microplus and *Haematobia irritans*.

According to the present invention, the veterinary composition comprises:
   a) At least one insect growth regulator compound (IGR). Examples include but are not limited to, at least one of the following: Diflubenzuron, cyromazine, triflumuron, methoprene, S-methoprene, hydroprene, S-hydroprene, fluazuron, dicyclanil, azadirachtin, lufenuron, flufenoxuron, nitenpyram, imidacloprid, teflubenzuron, noviflumuron, metoxifenozide, pyriproxyfen, tebufenozide, fenoxicarb, buprofezin, hexaflumuron, and/or a derivative thereof that is active, or any combinations thereof; and
   b) A micromineral mix. For instance, an iron, copper, cobalt, manganese, zinc, iodine, selenium and chromium micromineral mix, in their biologically absorbable forms. The micromineral mix can be in salt form; and optionally,
   c) At least one acceptable vehicle or carrier for its veterinary use.

According to the present invention, the veterinary composition can comprise:
   a) One or more compounds selected from the benzoyl substituted ureas defined in formula I below:

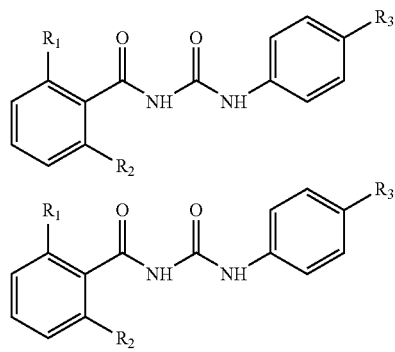

where:
$R_1$ and $R_2$ can be the same or different, and selected from halogen atoms or a methyl group, and being preferably fluorine (F) atoms.
$R_3$ can be selected from halogen atoms or alkyl groups containing 1 to 15 carbon atoms (e.g., from 1 to 10 carbon atoms, from 1 to 5 carbon atoms, such as 1, 2, 3, 4, 5, 6, 7, 8, 9, 10, 11, 12, 13, 14, or 15 carbon atoms), which could be optionally halogenated in one or more locations on the alkyl group. As a more specific example, $R_3$ is a chlorine atom. The alkyl group can be straight or branched. The alkyl group can be unsubstituted or substituted; and
   b) A micromineral mix. For instance, as described above or salt forms thereof. The salts that can comprise the micromineral mix are one or more among iron sulfate, copper sulfate, cobalt sulfate, manganese sulfate, potassium iodate, zinc oxide, and/or sodium selenite, or any combinations thereof; and optionally,
   c) At least one carrier acceptable to veterinary use.

Preferably, the composition of the present invention comprises the compound 1-(4-chloridephenyl)-3-(2,6-difluorobenzoyl)urea, also called diflubenzuron, and the micromineral mix (e.g., microminerals of iron sulfate, copper sulfate, cobalt sulfate, manganese sulfate, potassium iodate, zinc oxide and sodium selenite).

The compounds of Formula I above can be considered IGRs as well. The compounds of Formula I preferably have IGR activity.

For the compositions of the present invention, the composition can be prepared by mixing or otherwise combining the IGR or compounds of Formula I together, using any conventional mixing equipment. Preferably the ingredients are a simple mixture. Preferably, the ingredients are evenly distributed amongst each other to obtain a uniform mixture. The compositions, according to the present invention, present the advantage of simultaneously controlling ecto- and endoparasites in an efficient way, without substantially accumulating in the organisms of the animals and consequently without leaving residues that are hazardous to human health in meat or milk.

Regarding "controlling", this can include or refer to where 80% (by count) or more (e.g., at least 85%, at least 90%, at least 95%, at least 98%, at least 99%, about 100%, 100%) of the endoparasites and/or ectoparasites are reduced in population compared to a "control" where no treatment occurs. The "controlling" can include preventing larvae from turning into adult insects (larvicide) or by other mechanisms. Controlling can include or is keeping the ectoparasites and/or endoparasites at tolerable levels. For instance, in the case of bovine, where the milk production and/or weight and/or health of the bovine is not affected (e.g., by not more than 20% or not more than 10% for instance).

Regarding the micromineral mix (or mixture), this is or includes a reference to certain minerals found in trace amounts in an animal. Macrominerals are generally present at larger levels in the animal body or required in larger amounts in the diet. Macrominerals include calcium, chlorine, magnesium, phosphorus, potassium, sodium, and sulfur. On the other hand, microminerals are often referred to as trace minerals, meaning they are present at low levels in the body or required in smaller amounts in the animals diet. Microminerals can include chromium, cobalt, copper, fluorine, iodine, iron, manganese, molybdenum, selenium, and/or zinc. Micromineral in biology, means any chemical element required by living organisms in minute amounts, usually as part of a vital enzyme, a cell-produced catalytic protein. Exact needs vary among species, but commonly required plant micronutrients can include copper, boron, zinc, manganese, and/or molybdenum. Animals also can require manganese, iodine, and/or cobalt.

In the present invention, and as an option, the compositions of the present invention contain no macrominerals in the compositions and from a mineral point of view, can only contain microminerals and does not contain any macrominerals, except maybe for trace amounts. As an option, the macrominerals can be present in an amount of less than 0.0001% by weight, or 0% by weight, based on the total weight of the composition.

The efficient combat against the ecto- and endoparasites, for instance, ticks, horn flies and *Haemonchus* spp. is reached in a particular way with a dosage of active principle in the composition of the present invention, which varies according to the selected compounds. As an example, the present invention comprises from about 1 to about 10% in weight, such as from about 5 to about 7% in weight of at least one IGR compound or a benzoyl substitute urea of formula I (based on the total weight of the composition) and from about 0.01 to about 95% of a micromineral mix, such as selected from iron, copper, cobalt, manganese, zinc, iodine, selenium and/or chromium, among others. The micominerals can be in salt form. For example, the salts can be one or more among iron sulfate, copper sulfate, manganese sulfate, potassium iodate, zinc oxide and sodium selenite.

The optional vehicle or carrier is generally one that is considered acceptable carriers to veterinary use. According to the present invention, they can include all of those known in the art, for example: surfactants such as nonylphenol ethoxylate, sodium lignosulphonate, dodecyl benzene sulphonate, octylphenol ethoxylate, sodium polysorbate, potassium polysorbate, citric pectin, or sodium laurel sulphate, or solid carrier in particles such as micronized silica, kaolin or talc, or mixtures of them. Generally, the particles can be where 95% of the particles are 20 microns or less, though other sizes above this range can be used.

The composition of the present invention may also comprise one or more of thickening agents, stabilizers, flavoring agents, anticoagulants, preservatives and/or other adjuvants known in the art and in conventional amounts.

As far as another characteristic is concerned, the present invention is related to the use of benzoyl substituted ureas, associated with a micromineral mixture, as previously described, in the preparation of veterinary compositions against ectoparasites, more specifically horn flies and cattle ticks, and against endoparasites, more specifically *Haemonchus* spp., in bovines.

According to yet another characteristic, the present invention refers to a method of control of ectoparasites, which comprises the availability, via food or nutritional supplement, of an efficient daily amount of from about 20 to about 40 mg, preferably 30 mg, of at least one IGR compound or a benzoyl substituted urea of formula I, and from about 50 to about 80 mg of iron, from about 3 to about 7 mg of copper, from about 0.5 to about 4.5 mg of cobalt, from about 1 to about 5 mg of manganese, from about 2 to about 6 mg of iodine, from about 0.1 to about 0.5 mg of selenium, from about 0.1 to about 0.5 mg of chromium and/or from about 0.1 to about 2.0 mg of zinc.

The food made available to the animal can be, for example, grinded or pelletized. As it is well known by those skilled in the art, nutritional supplements can be one or more, without limitation, among mineralized salt, calcium phosphate, vitamin concentrations, protein supplements, and the like.

The quantity of the composition applied to the food or the nutritional supplement is established based on the predicted consumption for the food or supplement, which is well known in the cattle raising industry, for example:

Consumption of sodium chloride among bovines is 30 g/head of cattle/day. In this case it would be necessary to add the present invention in the following proportion: 302.5 g to each 25 kg of sodium chloride, being 103 mg/head of cattle/ the total daily intake of sodium chloride+the present invention.

In this case, the daily intake of one of the exemplified formulations can be as follows:

| | |
|---|---|
| Iron | 55.40 mg/head/day |
| Copper | 5.40 mg/head/day |
| Cobalt | 2.10 mg/head/day |
| Manganese | 3.20 mg/head/day |
| Iodine | 5.00 mg/head/day |
| Zinc | 1.30 mg/head/day |
| Selenium | 0.30 mg/head/day |
| Chromium | 0.30 mg/head/day |
| Diflubenzuron | 30.00 mg/head/day |

Other compositions of the present invention with different minerals and/or a different IGR compound or benzoyl substituted urea can produce similar results or results within 10% or 20% or 30% of these results.

According to one more characteristic, the present invention refers to a kit, characterized by the fact that it comprises a container (e.g., jar, bottle, can, bag or other type of container) containing the composition, a quantity dosing device and optionally instructions for its use in veterinary treatment of ectoparasites infestations, such as but not limited to tick infestations in bovines.

Herein under, some examples are presented of particular embodiments of the invention, and the scope of the invention is only limited by the claims hereof.

Example 1

Composition According to the Present Invention

Each 1,000 g of the present invention contains:

| | |
|---|---|
| Iron sulfate | 763.55 g |
| Copper sulfate | 60.0 g |
| Cobalt sulfate | 30.0 g |
| Manganese sulfate | 30.0 g |
| Potassium iodate | 20.0 g |
| Zinc Oxide | 10.0 g |
| Sodium selenite | 2.2 g |
| Chromium oxide | 1.6 g |
| Technical diflubenzuron | 82.65 g |

Test 1

Using Microminerals and Insect Growth Regulators in the Integrated Control of Parasites The experiment was conducted at Fazenda Santo Amaro in the city of Ouro Verde de Goiás—GO, Brazil, between October 2011 and January 2012, on 20 calves aged 12-16 months and weigh between 147 and 305 kg, divided in control group (T0) and treated group (T1).

The animals were weighed, identified and kept on *Brachiaha brizantha* pasture with "ad libitum" access to drinking water troughs. The control group received "ad libitum" minerals (T0), while the treated group received a micromineral mixture containing iron, copper, manganese, iodine, cobalt, zinc, selenium and chromium added to rock salt. Diflubenzuron was added to this mixture in the following proportion: 1.1 g per kilo of the mixture. A macromineral source was offered separately in the trough.

In order to determine the number of horn flies, ticks and helminth eggs per gram of feces, as well as periodic weighing, the animals were handled in a 30 day basis.

*Haematobia irritans*' Challenge

In Vitro Test

In order to evaluate the efficacy of Diflubenzuron over *H. irritans* larval development, without possible interference of climate changes, an experiment was conducted under controlled conditions.

Adult horn flies over untreated animals were captured with a net and then shipped to the Tropical Pathology and Public Health Institute (IPTSP/GO) in order to obtain the eggs. The flies were put on cages lined with moist coffee filter as a substrate for oviposition. The filter was inspected every three hours for eggs. Those were subject to analysis regarding viability and transferred to a vessel containing feces from 4 animals among the control and diflubenzuron treated groups, randomly chosen, each containing 50 viable eggs. These containers with feces were maintained in a B.O.D. incubator with constant temperature (25° C.) and under photoperiod of 12 hours, for a 20 day period, at the end of which was noted an end to the hatching of eggs.

The efficacy was proved by the relation between the number of adult horn flies obtained from each of the containers and the original number of eggs. Both groups—T0 e T1—, were statistically compared by the Mann-Whitney test, with P adjusted in 0.05 due to the impossibility of testing distribution normality, given the low number of repetitions (n=4).

Field Test

The animals were lead to the corral for the initial counting of the total number of horn flies in the cervical and lumbar regions. Both control (T0) and diflubenzuron treated (T1) groups showed statistically similar average parasite infestation (C=474.5±123.8; T=465.0±125.2; t=0.2425 and P=0.8097).

*Rhipicephalus* (*Boophilus*) Microplus' Challenge

For this challenge, 5 animals were randomly selected from each group. Animals from both control and treated groups were transferred to individual tick-free pens with wooden tiled floor, where they remained for 21 days until the engorged females dropped to the ground. Those were collected on a daily basis for a 5 day period, and put on plastic vessels, formerly washed and dried with paper towels. After the engorged ticks were weighed, they're put on Petri dishes and then into a B.O.D. incubator for two weeks, under 27° C. and relative humidity over 85% (SANTOS e FURLONG, 2002; PEREIRA, 2006).

After this period, oviposition in each of the Petri dishes were weighed and transferred to assay tubes (15 cm high and with a 15 mm diameter each) sealed with cotton. The assays tubes were labeled and then returned to the B.O.D. incubator, under the same conditions described above, up to the larval emergence.

Gastrointestinal Worms' Challenge

The animals had their fecal samples collected straight from the rectum prior to the EPG count. Labeled samples in the veterinary gloves were kept on ice and then sent to the Parasitology Department lab of the Tropical Pathology and Public Health Institute (IPTSP) at Goiás State Federal University, Brazil, to be subjected to the modified GORDON & WITHLOCK (1939) test.

To determine the number of eggs per gram of feces (EPG) and live weight follow-up, animals were handled every 30 days.

The day before the end of the experiment, feces were collected for EPG count and weighing. After a 12 hour fasting on the last day, the calves were slaughtered at Anápolis—GO, Brazil.

After the opening of the thoracic and abdominal cavities, dual bandages were made with the aid of a string between rear end of reticulum and upper end of abomasum; rear end of abomasum and upper end of the small intestine, and finally between the rear end of the small intestine and upper end of large intestine (UENO & GONÇALVES, 1998). The organs were put in separate plastic bags inside ice boxes, labeled and sent to the lab for a post-mortem examination.

Statistical analysis of the results was performed with GraphPad Prism v. 5.04 software, with P adjusted to 0.05.

Discussion

*Haematobia irritans*

The in vitro evaluation ended after 20 days of development. The control group had a hatching average of 43±4.1633, while the group cultivated in the feces of cattle treated with Diflubenzuron presented a hatching average of only 0.5±0.1. According to the methodology proposed by HOLDSWORTH et al., 2006, the calculated efficiency, based on the control group, was of 98.83%. Using the Mann-Whitney test, there was a noticeable statistical difference between the groups (U=0.0; P=0.0265).

Field Test

The field experiment was conducted during the summer, a critical period for horn fly infestations in Brazil (BIANCHIN et al., 2004). At the beginning of the experiment, there was no noticeable statistical difference between the two groups, whose average infestations were equivalent (C1=474.5±123.8 and T1=465.0±125.2). During the experimental period, the handlers reported an noticeable reduction on horn fly numbers on the treated group, while the animals of the control group remained under constant harassment by the horn flies, showing clear signs of annoyance.

At the end of the experimental period, the animals were lead to the containment chute to have the flies counted. There was no significant reduction on the control group (t=07307, P=0.4694). As for the treated group, there was a clear reduction on *H. irritans* infestation (t=16.46, P<0.0001). There was also observed statistical difference between final times among both groups (t=15.75; P<0.0001). Under field conditions, the product's efficacy was 99.20%.

According to GROSSCURT (1978), Diflubenzuron acts on all larval stages of insects, but with some species, first and last stages can be less susceptible. In turn, KUNZ et al. (1976), observed that this molecule could also be absorbed by female arthropods, interfering in the reproductive processes so as to affect embryos and hamper most of larval emergence. The in vitro test of the present work clearly demonstrated the action of this molecule's presentation over the development of immature forms, confirming the excretion of the still active molecule among the animal's feces, besides excellent efficacy on the field test, on which it was observed higher than 99% reduction on horn fly numbers on the treated group.

In 2002, SILVA & MENDES observed that not only the third larval instar was more sensible to diflubenzuron's action, but cited Hopkins and Chamberlain (1976), who reported the presence of malformed *H. irritans* pupae derived from larvae reared continuously in medium treated with diflubenzuron. According to EISLER (1992), at extremely low doses diflubenzuron selectively inhibits the ability of arthropods to synthesize chitin at the time of molting, killing the organism from rupture of the cuticle or starvation. Other organisms that contain chitin (i.e., some species of fungi and marine diatoms), or polysaccharides similar to chitin (i.e., birds and mammals), seem unaffected.

Diflubenzuron's efficacy results were also confirmed regarding control of insects relevant to public health, such as *Aedes aegypti* (BORGES et al, 2004; MARTINS and SILVA, 2004), *Culex quinquefasciatus* and *pipiens* (SELF et al, 1978; HAJJAR, 1979), *Musca domestica* (MILLER et al., 1975; ABLES, 1975) and *Anopheles dariingi* (COSTA, 2007).

*Rhipicephalus* (*Boophilus*) Microplus

The weight of the engorged ticks collected among animals from the control group was around 260-295 mg, which according to literature is the normal weight of healthy engorged female ticks.

Among the group treated with diflubenzuron, the collected engorged ticks weighed 145-165 mg, i.e., short from the standard.

The average engorged female ticks' weight on the treated and control groups was 153 mg e 278 mg, respectively, showing there was significant statistical difference (p<0.005) between groups.

The average egg laying of the female *Rhipicephalus* (*Boophilus*) microplus on the control and treated groups was 2,600 and 900 eggs, respectively.

Even if not with a knock-down effect, the results of this work, namely the reduction on engorged female ticks and its eggcide action, prove diflubenzuron's efficacy on controlling *Rhipicephalus* (*Boophilus*) microplus.

Gastrointestinal Worms

Regarding the weight of the animals, statistical analysis revealed great difference between the group treated with the micromineral mixture (F=8.732; P=0.0002) when compared to the control group, which didn't present significant difference in the duration of the experimental period (F=2.821; P=0.525). Although the comparison between the averages of initial weight (Pi) and final weight (Pf) of both groups on test t didn't have shown relevant difference (Pi-1=0.4038; GL=18; P=0.6911; Pf-t=1.590; GL=18; P=0.1292), there was a numeric difference of 15 kg. Regarding the EPG, statistical difference was found by the ANOVA test followed by Tukey throughout the experimental period for both groups (treated group→F=56.95; P<0.0001/control group→F=3.087; P=0.0393), although for the control group the test showed difference only between the initial count and the 60 day count. Comparison of the initial and final count average between groups by test t revealed that in the beginning of the experimental period both groups showed equivalent averages (t=0.5695; GL=18; P=0.5761), while the final averages of this parameter were clearly different (t=7.609; GL=18; P<0.0001).

Comparison of the helminth average obtained after necropsies revealed great difference concerning the three diagnosed genres, confirming the treatment's effect over this parameter (*Haemonchus* U=0.0000; P=0.0002; *Trichostrongylus* U=5.000; P=0.0007; *Oesophagostomum* U=3.000; P=0.0004).

When ROCHA (1951) compared the results of various drug combinations, he concluded that the synergic action of iron, copper and other minerals, when administered with the regular rock salt feed, combined two advantages: expelling nematodes and fighting anemia.

The weight gain of 15 kg observed among bovines is as expected. Such effect had already been observed by FIGUEIREDO et al. (1972), VIEIRA (1973), PINHEIRO, 1985; SOUTELLO, 2001; CABRAL (2007).

The results obtained after the present experiment showed once again the controlling action of the micromineral compound over the population of gastrointestinal triconstrongylus, namely those with hematophagous habits (FERRARI, 1972; FIGUEREDO et al., 1972; VIEIRA, 1973;

GONçALVES, 1976; SILVA and QUINTANA, 1976; CABRAL, 2007; DELL'PORTO et al., 2009; VILELA, 2011), and that the reduction of the nematode population also depends on the betterment of the overall state of the host.

CONCLUSION

Besides the ease of administration and efficacy, it's been also proved that the micromineral mixture with diflubenzuron didn't show chemical residues in the final product, according to TFOUNI et al. (2007), being unnecessary a withdrawal period for both beef and milk—an important fact for public health. An integrated parasite control program, with mineral supplementation rich in, namely, iron and copper, mixed with IGRs, is a rational and less stressful mean of treating cattle, especially when aiming higher weight gain rates in shorter periods.

Under the experimental conditions, the micromineral and diflubenzuron compound added to rock salt showed efficacy on treating the main cattle parasites.

Based on the results described herein, one can verify that the present invention composition, as well as the method of treatment, is highly efficient on controlling tick infestations on cattle, besides presenting several technical and economic advantages.

From the data and information presented herein, a person skilled in the art could use this invention in several ways, in a non-identical manner to what was described hereby, but with the functionality and result described herein, being, therefore, within the scope of the attached claims.

The invention claimed is:

1. A veterinary composition for controlling ecto- and endoparasites in animals, comprising at least one IGR compound, a micromineral mix comprising each of the microminerals iron, copper, cobalt, manganese, iodine, selenium, chromium, and zinc, and optionally at least one carrier, wherein said veterinary composition comprises from about 20 to about 40 mg of at least one IGR compound, from about 50 to about 80 mg of iron, from about 3 to about 7 mg of copper, from about 0.5 to about 4.5 mg of cobalt, from about 1 to about 5 mg of manganese, from about 2 to about 6 mg of iodine, from about 0.1 to about 0.5 mg of selenium, from about 0.1 to about 0.5 mg of chromium, and from about 0.1 to about 2 mg of zinc per 103 mg combined weight of the at least one IGR compound, iron, copper, cobalt, manganese, iodine, selenium, chromium, and zinc in the composition.

2. A veterinary composition for controlling ecto- and endoparasites in animals, comprising a) at least one benzoyl substituted urea, according to formula I:

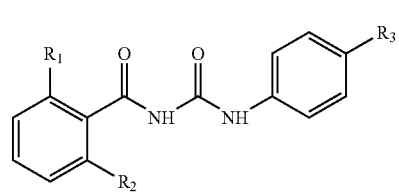

where:
R$^1$ and R$^2$, which are the same or different, is an halogen atom or a methyl group,
R$^3$ is an halogen atom or an alkyl group containing 1 to 15 carbon atoms, optionally halogenated;

b) a micromineral mix comprising each of the microminerals iron, copper, cobalt, manganese, iodine, selenium, chromium, and zinc; and c) optionally, at least one carrier acceptable to veterinary use, wherein said veterinary composition comprises from about 20 to about 40 mg of at least one benzoyl substituted urea according to formula I, from about 50 to about 80 mg of iron, from about 3 to about 7 mg of copper, from about 0.5 to about 4.5 mg of cobalt, from about 1 to about 5 mg of manganese, from about 2 to about 6 mg of iodine, from about 0.1 to about 0.5 mg of selenium, from about 0.1 to about 0.5 mg of chromium, and from about 0.1 to about 2 mg of zinc per 103 mg combined weight of the at least one benzoyl substituted urea, iron, copper, cobalt, manganese, iodine, selenium, chromium, and zinc in the composition.

3. The veterinary composition according to claim 2, wherein R$^1$ and R$^2$ are fluorine atoms and R$^3$ is a chlorine atom.

4. The veterinary composition according to claim 1, wherein the IGR compound is 1-(4-chloridephenyl)-3-(2,6-difluorobenzoyl)urea.

5. The veterinary composition according to claim 1, wherein the IGR compound is diflubenzuron, cyromazine, triflumuron, methoprene, S-methoprene, hydroprene, S-hydroprene, fluazuron, dicyclanyl, azadirachtin, lufenuron, flufenuxuron, nitenpiram, imidacloprid, teflubenzuron, noviflumuron, methoxyfenozide, pyriproxyfen, tebufenozide, fenoxycarb, buprofezin, hexaflumuron, a chemically active derivative thereof, or any combinations thereof.

6. The veterinary composition according to claim 1, wherein said carrier is a nonylphenol ethoxylate, sodium lignosulphonate, dodecyl benzene sulphonate, octylphenol ethoxylate, sodium polysorbate, potassium polysorbate, citric pectin, sodium laurel sulphate, micronized silica, kaolin, or talc, or any combinations thereof.

7. The veterinary composition according to claim 1 further comprising at least one thickening agent, at least one stabilizer, at least one flavoring agent, at least one anticoagulant, or at least one preservative, or any combinations thereof.

8. A method to control ecto- and endo-parasites, comprising administering the veterinary composition of claim 1 to an animal in an amount effective to control said ecto- and endo-parasites.

9. A method to control ecto- and endo-parasites, comprising administering the veterinary composition of claim 2 to an animal in an amount effective to control said ecto- and endo-parasites.

10. A kit for the control method of ectoparasites, comprising at least the veterinary composition of claim 1 in at least one container, a quantity dosing device, and optionally instructions for administering said composition.

11. A method for controlling ecto- and endoparasites and enhancing zootechnical performance, comprising administering, orally, through feed or nutritional supplementation, the veterinary composition of claim 1 whereby control of ecto- and endoparasites is achieved.

12. The veterinary composition of claim 1, wherein said veterinary composition does not comprise of macrominerals.

13. The veterinary composition of claim 1, wherein said veterinary composition comprises macrominerals in an amount of less than 0.0001% by weight, based on the total weight of the composition.

14. The veterinary composition of claim 1, wherein said veterinary composition does not comprise thickening agents.

15. The veterinary composition of claim 1, wherein said veterinary composition does not comprise thickening agents, stabilizers, flavoring agents, anticoagulants, preservatives and adjuvants.

16. The veterinary composition of claim 1, wherein said veterinary composition does not comprise thickening agents and carriers.

* * * * *